United States Patent [19]

Kishi et al.

[11] 4,108,861
[45] Aug. 22, 1978

[54] AZETOTHIAZOLE-5-YL-3-HALOMETHYL-2-BUTENOIC ACID DERIVATIVES AND THE PREPARATION OF 5-THIA-1-AZABICYCLO-[4.2.0]-2-OCTENE-2-CARBOXYLIC ACID DERIVATIVES FROM THEM

[75] Inventors: Yoshito Kishi; Shinichi Nakatsuka; Hideo Tanino, all of Cambridge, Mass.

[73] Assignee: Fujisawa Pharmaceutical Co., Ltd., Osaka, Japan

[21] Appl. No.: 781,582

[22] Filed: Mar. 28, 1977

Related U.S. Application Data

[63] Continuation of Ser. No. 627,577, Oct. 31, 1975, abandoned.

[30] Foreign Application Priority Data

Nov. 6, 1974 [JP] Japan .................. 49-128477

[51] Int. Cl.² .................. C07D 513/04; C07D 501/02
[52] U.S. Cl. .................. 260/306.7 C; 544/21; 560/155; 560/170; 560/172
[58] Field of Search .................. 260/243 C, 306.7 C; 544/21

[56] References Cited

U.S. PATENT DOCUMENTS 3,705,892  12/1972  Cooper .................. 260/306.7 C
3,880,872  4/1975  Kukolja et al. .................. 260/306.7 C

OTHER PUBLICATIONS

Baldwin et al., J. Am. Chem. Soc. 95(7), pp. 2401–2403, 4/4/73.

Primary Examiner—Donald G. Daus
Assistant Examiner—Diana G. Rivers
Attorney, Agent, or Firm—Bierman & Bierman

[57] ABSTRACT

A compound of the formula

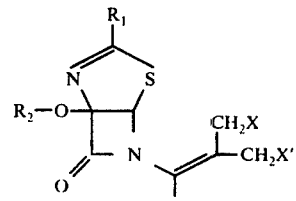

wherein
$R_1$ is lower alkyl, aryloxy(lower)alkyl or ar(lower)alkyl,
$R_2$ is lower alkyl,
$COOR_3$ is esterified carboxy selected from lower alkoxycarbonyl and ar(lower)alkoxycarbonyl,
X is halogen selected from bromine and chlorine, and
X' is hydrogen or halogen selected from bromine and chlorine,
said aryl and said ar each constituting phenyl, tolyl or xylyl, and a method of making it are disclosed.

14 Claims, No Drawings

AZETOTHIAZOLE-5-YL-3-HALOMETHYL-2-BUTENOIC ACID DERIVATIVES AND THE PREPARATION OF 5-THIA-1-AZABICYCLO-[4.2.0]-2-OCTENE-2-CARBOXYLIC ACID DERIVATIVES FROM THEM

This application is a Rule 60 continuation of copending Ser. No. 627,577 filed Oct. 31, 1975, now abandoned, which claimed the priority of Japanese Ser. No. 128,477, filed on Nov. 6, 1974 — both priorities of which are hereby claimed.

This invention relates to a new process for the preparation of 5-oxa(or thia)-1-azabicyclo[4,2,0]-2-octene-2-carboxylic acid derivatives. More particularly, it relates to novel intermediates, 2-[3a, 5a-dihydro-4H-azeto[3,2-d]oxazol(or thiazol)-5-yl]-3-halomethyl-2-butenoic acid derivatives, a process for the preparation thereof and a new process for the preparation of 5-oxa(or thia)-1-azabicyclo[4,2,0]-2-octene-2-carboxylic acid derivatives which are useful as antimicrobial agents.

The processes for the preparation of the intermediates and the final products of the present invention are illustrated by the following reaction scheme.

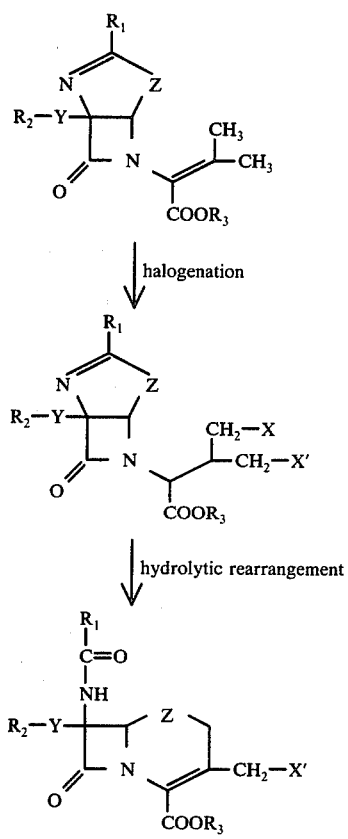

wherein
$R_1$ is lower alkyl, aryloxy(lower)alkyl or ar(lower)alkyl,
$R_2$ is lower alkyl
$COOR_3$ is esterified carboxy,
X is halogen,
X' is hydrogen or halogen, and Y and Z are each oxy or thio.

In the above definition of the symbols, it is to be understood that the term "lower" is intended to mean 1 to 6 carbon atoms.

Suitable examples of "lower alkyl" for $R_1$ and $R_2$ may be methyl, ethyl, propyl, isopropyl, butyl, isobutyl, tert-butyl, pentyl, hexyl and the like.

Suitable examples of "aryloxy(lower)alkyl" may be phenoxymethyl, phenoxyethyl, phenoxypropyl, phenoxybutyl, tolyloxymethyl, xylyloxymethyl and the like.

Suitable examples of "ar(lower)alkyl" may be benzyl, phenethyl, phenylpropyl, tolylmethyl, xylylmethyl and the like.

Suitable examples of "halogen" for X and X' may be chlorine, bromine and the like.

Suitable examples of "esterified carboxy" may be lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, etc.), ar(lower)alkoxycarbonyl (e.g. benzyloxycarbonyl, phenethyloxycarbonyl, diphenylmethoxycarbonyl, phenylpropoxycarbonyl, etc.) and the like.

The starting compounds of the present invention can be prepared by the following new processes:

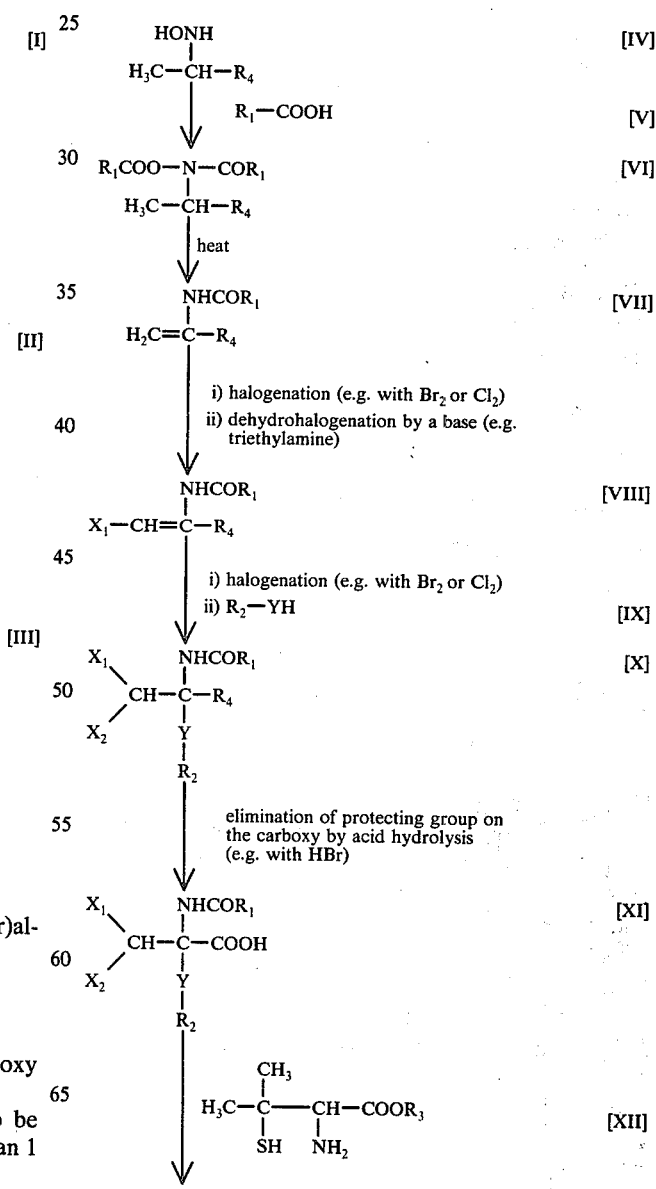

-continued

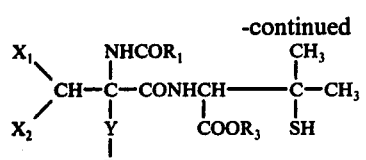

i) an organic sulfonic acid or its reactive derivative (e.g. toluene sulfonic acid chloride
ii) a base (e.g. triethylamine)

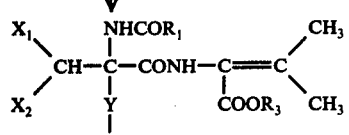

phosphorus pentasulfide followed by a base (e.g. sodium hydride)

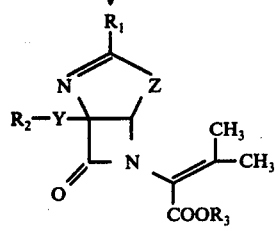

wherein
$R_4$ is protected carboxy (e.g. lower alkoxy carbonyl),
$X_1$ and $X_2$ are halogen, and
$R_1$, $R_2$, $COOR_3$, Y and Z are each as previously defined herein.

Among these starting compounds [I], 2-[3a, 5a-dihydro-4H-azeto[3,2-d]oxazol-5-yl]-3-methyl-2-butenoic acid derivatives [I], wherein Z is oxy, can be prepared by treating a compound [XIV] with a base, and 2-[3a,5a-dihydro-4H-azeto[3,2-d]thiazol-5-yl]-3-methyl-2-butenoic acid derivatives [I], wherein Z is thio, can be prepared by treating a compound [XIV] with phosphorus pentasulfide and then with a base.

The intermediates [II] of the present invention can be prepared by halogenation of starting compound [I]. The halogenation may be carried out by treating a compound [I] with a halogenating agent such as N-halogenophthalimide or N-halogenosuccinimide (e.g. N-bromosuccimimide, N-chlorosuccimide, N-bromophthalimide etc.), N-halogenohydantion (e.g. N-bromohydantion etc.), N-halogenocaprolactam (e.g. N-bromocaprolactam etc.), or the like. The reactions are usually carried out in a conventional solvent such as methylene chloride, chloroform, carbon tetrachloride, ethylene chloride or the like which does not interfere with the reaction, during heating or at somewhat elevated temperatures. The reaction product [II] can be isolated and purified in a conventional manner, for example by extraction, chromatography or the like. Alternatively, the intermediate produced in this reaction may be subjected to the following hydrolytic rearrangement without the necessity of isolation or purification as above.

A compound of the formula:

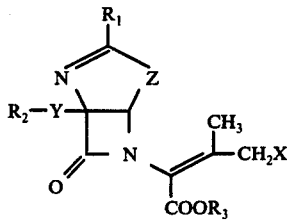

wherein $R_1$, $R_2$, $COOR_3$, X, Y and Z are each as defined above, is sometimes produced as a by-product of the above reaction but by further halogenation, which may be transformed into the intermediate [II] wherein X and X' are both halogen.

The intermediates [II] thus obtained are used in the hydrolytic rearrangement process for the preparation of compounds [III].

The compounds [III] may be prepared by hydrolytic rearrangement of the intermediates [II].

The rearrangement may be carried out easily and conveniently by merely allowing a solution of compound [II] to stand in a conventional solvent (such as methylene chloride or the like), in an unsealed vessel at ambient temperatures.

The product [III] thus produced can be isolated from the reaction mixture and purified in a conventional manner.

EXAMPLE (A) Preparation of the Starting Compound (1) tert-Butyl ester of N-acetyl-N-acetoxyalanine 17.7 g. of the tert-butyl ester of N-hydroxyalanine which was prepared from tert-butyl bromopropionate by the method of Newman et al. [J. Amer. Chem. Soc. 77, 2308 (1971)] was added to 40 ml. of acetic anhydride and the mixture was stirred for 30° minutes at 100° C. The reaction mixture was evaporated to dryness under reduced pressure to give the oily tert-butyl ester of N-acetyl-N-acetoxyalanine.

N.M.R.: δ (CDCl₃)ppm: 1.39 (3H, d, J=7Hz), 1.46 (9H, s), 2.09 (3H, s) 2.23 (3H, s), 5.10 (1H, q, J=7Hz).

(2) tert-Butyl 2-acetamidoacrylate

The tert-butyl ester of N-acetyl-N-acetoxyalanine obtained above was dissolved in a mixture of 200 ml. of benzene and 40 ml. of triethylamine and the solution was refluxed for 2 hours. The reaction mixture was concentrated by evoporation under reduced pressure. The residue was filtered through a short column packed with silica gel to give 14.7 g. of oily tert-butyl 2-acetamidoacrylate.

N.M.R.: δ (CDCl₃)ppm: 1.53 (9H, s), 2.13 (3H, s), 5.89 (1H, s), 6.61 (1H, s), 7.96 (1H, broad s).

(3) tert-Butyl-2-acetamido-3-bromoacrylate 14.7 g. of the tert-butyl 2-acetamidoacrylate obtained above was dissolved in 100 ml. of methylene chloride. To the solution was added dropwise a solution of 1.270 g. of bromine in 10 ml. of methylene chloride in about 20 minutes, and then 11 ml. of triethylamine was added to the mixture. The mixture was allowed to stand for 30 minutes at ambient temperature. 50 ml. of ether was added to the mixture and the precipitates were filtered off with suction and washed with ether. The filtrate and the washings were combined, washed twice with 1N hydrochloric acid and then with saturated aqueous sodium chloride. The aqueous layer was extracted three times with methylene chloride. The extract was combined with the ether layer obtained above, dried over sodium sulfate and concentrated under reduced pressure. The residue was filtered through a short column packed with silica gel and the filtrate was crystallized by treating with a mixture of ether and hexane to give 17.93 g. of tert-butyl 2-acetamido-3-bromoacrylate having a m.p. of 106°–107° C.

Analysis: Calcd. for $C_9H_{14}NO_3Br$: C, 40.92; H, 5.34; N, 5.30: Found: C, 41.06; H, 5.31; N, 5.33.

N.M.R. δ ($CDCl_3$)ppm: 1.51 (9H, s), 2.16 (3H, s), 7.17 (1H, s), 7.55 (1H, broad s).

I.R.: $\nu_{max}^{KBr}$ cm$^{-1}$: 1710, 1665, 1620, 1520.

(4) tert-Butyl 2-methoxy-2-acetamido-3,3-dibromopropionate 300 mg. of tert-butyl 2-acetamido-3-bromoacrylate was dissolved in 6 ml. of methylene chloride. 3.16 ml. of a solution containing 538 mg. of bromine per 10 ml. of methylene chloride was added dropwise to the solution obtained above at 0° C over a period of 10 minutes and the resultant mixture was allowed to stand for 20 minutes at ambient temperature, 3 ml of methanol was added to the mixture and it was allowed to stand for an additional 40 minutes at ambient temperature. The reaction mixture was diluted with methylene chloride and then washed with saturated aqueous sodium bicarbonate. The aqueous layer was extracted four times with methylene chloride. The extracts were combined with the methylene chloride solution obtained above, the total solution was dried over sodium sulfate and evaporated to dryness under reduced pressure. The residue was crystallized by treating with a mixture of ether and hexane to give 348 mg. of tert-butyl 2-methoxy-2-acetamido-3,3-dibromopropionate having a m.p. of 115°–116° C.

N.M.R.: δ ($CDCl_3$)ppm: 1.56 (9H, s), 2.12 (3H, s), 3.44 (3H, s), 6.38 (1H, s), 6.59 (1H, broad s).

I.R.: $\nu_{max}^{KBr}$ cm$^{-1}$: 3355, 1745, 1695, 1510, 1150.

(5) 2-Methoxy-2-acetamido-3,3-dibromopropionic acid 300 mg. of tert-butyl 2-methoxy-2-acetamido-3,3-dibromopropionate was added to 5 ml. of methanol saturated with hydrogen bromide. The mixture was stirred for 70 minutes at 60° C. and then evaporated to dryness under reduced pressure. The residue was treated with benzene to give crystalline 2-methoxy-2-acetamido-3,3-dibromopropionic acid having a m.p. of 143°–144° C.

Analysis: Calcd for $C_6H_9NO_4Br_2$: C, 22.59; H, 2.84; N, 4.39: Found: C, 22.48; H, 2.80; N, 4.34.

N.M.R.: δ ($CD_3OD$)ppm: 2.08 (3H, s), 3.46 (3H, s), 6.32 (1H, s).

(6) Methyl ester of N-(2-methoxy-2-acetamido-3,3-dibromopropionyl)-penicillamine A mixture of 100 mg. of 2-methoxy-2-acetamido-3,3-dibromopropionic acid and 148 mg. of dicyclohexylcarbodiimide in 20 ml. of dioxane was stirred for an hour at ambient temperature. To the mixture was added a mixture of 75.2 mg. of the methyl ester of DL-penicillamine hydrochloride and 52.5 μl. of triethylamine in 2 ml. of dioxane, and the mixture was stirred for 12 hours at ambient temperature. The precipitates were filtered off and washed with ether. The filtrate and the washings were combined and concentrated under reduced pressure. The residue was fractionated by subjecting it to a preparative thin layer chromatography on silica gel and crystallized from a mixture of ether and hexane to give 77 mg. of the crystalline methyl ester of N-(2-methoxy-2-acetamido-3,3-dibromopropionyl)penicillamine.

Analysis: Calcd. for $C_{12}H_{20}N_2O_5SBr_2$: C, 31.12; H, 4.13; N, 6.05: Found: C, 30.97; H, 4.48; N, 6.36.

(7) Methyl 2-(2-methoxy-2-acetamido-3,3-dibromopropionamido)-3-methyl-2-butenoate.

A mixture of 1500 mg. of the methyl ester of N-(2-methoxy-2-acetamido-3,3-dibromopropionyl)penicillamine and 415 mg. of p-toluenesulfonyl chloride in 10 ml. of pyridine was allowed to stand for 3 hours at ambient temperature. After the resultant solution was diluted with methylene chloride, the pyridine was removed by washing with 1N hydrochloric acid. The washings were extracted four times with methylene chloride. The extracts and the organic layer obtained above were combined and concentrated under reduced pressure. The residue was subjected to column chromatography on silica gel to give 568 mg. of an oily product. The oily product was dissolved in 50 ml. of triethylamine and stirred for 12 hrs. at 80° C. The reaction mixture was evaporated to dryness under reduced pressure, and treated with a mixture of methylene chloride and saturated aqueous sodium chloride. After the organic layer was separated, the aqueous layer was extracted with methylene chloride. The organic layer and the extracts were combined, dried, and concentrated under reduced pressure. The residue was subjected to column chromatography on silica gel and then crystallized from a mixture of ether and hexane to give 194 mg. of methyl 2-(2-methoxy-2-acetamido-3,3-dibromopropionamido)-3-methyl-2-butenoate having a m.p. of 150°–151° C.

N.M.R.: δ ($CDCl_3$)ppm: 202 (3H, s), 2.12 (3H, s), 2.26 (3H, s), 3.43 (3H, s), 3.79 (3H, s), 6.87 (1H, s), 7.20 (1H, broad s), 7.96 (1H, broad s).

I.R.: $\nu_{max}^{KBr}$ cm$^{-1}$: 3340, 1730, 1695, 1675, 1485.

(8) Methyl 2-(2-methyl-3a-methoxy-4-oxo-3a,5a-dihydro-4H-azeto[3,2-d]thiazol-5-yl)-3-methyl-2-butenoate A suspension of 25 mg. of the methyl 2-(2-methoxy-2-acetamido-3,3-dibromopropionamido)-3-methyl-2-butenoate obtained above and 76 mg. of phosphorus pentasulfide in 2.5 ml. of tetrahydrofuran was stirred for 2 hours at 50° C. After cooling, the resultant mixture was diluted with methylene chloride, and shaken with a mixture of saturated aqueous solution of sodium chloride and sodium bicarbonate (each 10 ml.). The organic layer was separated and the aqueous layer was washed three times with methylene chloride. The organic layer and the washings were combined, dried over sodium sulfate, and concentrated under reduced pressure. The residue was dissolved in methylene chloride and the insoluble substances were filtered off. The filtrate was evaporated to dryness under reduced pressure and then dried in a evacuated desicator for 30 minutes to give an oily product. To the oil were added 2.5 ml. of tetrahydrofuran and 20.3 mg. of a dispersion of 66% of sodium hydride in mineral oil and stirred for 3 hours at ambient temperature under a nitrogen atmosphere. To the solution was added 30 μl of acetic acid and stirred for 15 minutes. The resultant solution was diluted with methylene chloride, and shaken with a mixture of saturated aqueous solution of sodium chloride and sodium bicarbonate. After the organic layer was separated, the aqueous layer was extracted three times with methylene chloride. The organic layer and the extracts were combined, dried over sodium sulfate, and then concentrated under reduced pressure to give an oily residue. The oily residue was fractionated by preparative thin layer chromatography on alumina to give 2 mg. of oily methyl 2-(2-methyl-3a-methoxy-4-oxo-3a, 5a-dihydro-4H-azeto[3,2-d]thiazol-5-yl)-3-methyl-2-butenoate.

N.M.R.: δ (CDCl$_3$)ppm: 1.82 (3H, s), 2.27 (3H, s), 2.38 (3H, s), 3.62 (3H, s), 3.80 (3H, s), 5.82 (1H, s).

I.R.: $\nu_{max}^{CH_2Cl_2}$ cm$^{-1}$: 1775, 1728, 1618.

(B) Preparation of Intermediate Compound [II]

(1) A mixture of 40.7 mg. of methyl 2-(2-methyl-3a-methoxy-4-oxo-3a,5a-dihydro-4h-azeto[3,2-d]thiazol-5-yl)-3-methyl-2-butenoate, 31 mg of N-bromosuccinimide, and 21 mg. of α,α'-azabisisobutyronitrile in 12 ml. of carbon tetrachloride was stirred for 1.5 hours at 75° C. After cooling, the reaction mixture was diluted with methylene chloride and shaken with a mixture of saturated aqueous solutions of sodium chloride and sodium sulfite. After the organic layer was separated, the aqueous layer was extracted four times with methylene chloride. The organic layer and the extracts were combined together and concentrated under reduced pressure. The residue was fractionated by thin layer chromatography on alumina to give 28.3 mg. of an about 2:3 mixture of two geometrical isomers of methyl 2-(2-methyl-3a-methoxy-4-oxo-3a,5a-dihydro-4H-azeto[3,2-d]thiazol-5-yl)-3-bromomethyl-2-butenoate and 5.3 mg. of methyl 2-(2-methyl-3a-methoxy-4-oxo-3a,5a-dihydro-4H-azeto[3,2-d]thiazol-5-yl)-3-dibromomethyl-4-bromo-2-butenoate. Each isomer of the mono-bromo compound was separated by subjecting the isomeric mixture to high pressure liquid chromatography under the following conditions. [stationary phase, CORASIL-I, column: inch × 2 feet, column press: 200 psi, flow rate: 1 ml./min, mobile phase: ethyl acetate (1 part) and hexane (12 parts)] to give 2 parts of the isomer having the formula [IIa]:

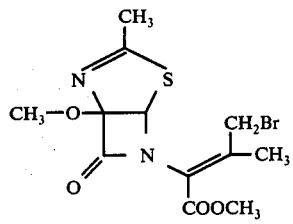

[IIa]

(retention time: 15 minutes), and 3 parts of the isomer having the formula [IIb]:

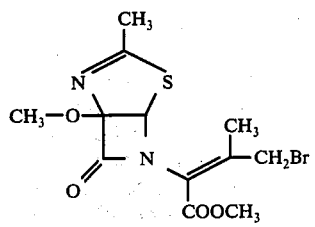

[IIb]

(retention time: 20 minutes)

The isomer having the formula [IIa]:

N.M.R. δ (CDCl$_3$)ppm: 2.33 (3H, s), 2.41 (3H, s), 3.62 (3H, s), 3.82 (3H, s), 3.92 (2H, s), 5.82 (1H, s).

The other isomer having the formula [IIb]

N.M.R.: δ (CDCl$_3$)ppm: 1.95 (3H, s), 2.39 (3H, s), 3.62 (3H, s), 3.85 (3H, s), 4.28 (1H, AB, J=10Hz), 4.73 (1H, AB, J=10Hz), 5.82 (1H, s).

The dibromo compound:

N.M.R.: δ (CDCl$_3$)ppm: 2.48 (3H, s), 3.64 (3H, s), 3.92 (3H, s), 4.16 (2H, s), 4.51 (1H, AB, J=10Hz), 4.79 (1H, AB, J=10Hz), 5.87 (1H, s).

I.R.: $\nu_{max}^{CH_2Cl_2}$ cm$^{-1}$: 1785, 1732, 1615.

(C) Preparation of compound [III]

A solution of the 11 mg. of the isomer of methyl 2-(2-methyl-3a-methoxy-4-oxo-3a,5a-dihydro-4H-azeto[3,2-d]thiazol-5-yl)-3-bromomethyl-2-butenoate having the formula [IIa] in 100 ml. of methylene chloride was devided into 50 portions and each portion was placed in a small unsealed flask and allowed to stand for 3 days at 20° C.

All the portions were combined and concentrated under reduced pressure.

The residue was subjected to preparative thin layer chromatography on silica gel [developing solvent: methanol (5 parts) and methylene chloride (95 parts)] to give 4 mg. of methyl 7-acetamido-7-methoxy-3-methyl-3-cephem-4-carboxylate.

N.M.R.: δ (CDCl$_3$)ppm: 2.15 (6H, broad s), 3.17, 3.44 (1H, 1H, AB, J=18Hz), 3.86 (3H, s), 5.10 (1H, s), 7.18 (1H, broad s).

I.R.: $\nu_{max}^{CH_2Cl_2}$ cm$^{-1}$: 3420, 1777, 1731, 1705.

What we claim is:

1. A compound of the formula

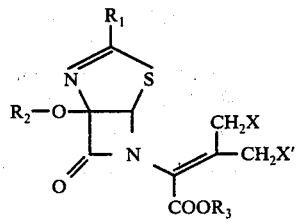

wherein

R$_1$ is lower alkyl, aryloxy(lower)alkyl or ar(lower)alkyl,

R$_2$ is lower alkyl,

COOR$_3$ is esterified carboxy selected from lower alkoxycarbonyl and ar(lower)alkoxycarbonyl, X is halogen selected from bromine and chlorine, and X' is hydrogen or halogen selected from bromine and chlorine, said aryl and said ar each constituting phenyl, tolyl or xylyl.

2. A compound according to claim 1 in which R$_1$ and R$_2$ are each lower alkyl and COOR$_3$ is lower alkoxycarbonyl.

3. A compound according to claim 2 in which R$_1$ and R$_2$ are each methyl and X' is hydrogen.

4. A compound according to claim 3 in which X is bromine.

5. A compound according to claim 2 in which R$_1$ and R$_2$ are each methyl and COOR$_3$ is methoxycarbonyl.

6. A compound according to claim 5 in which X and X' are each bromine.

7. A process for the preparation of a compound according to claim 1, which comprises treating a compound of the formula:

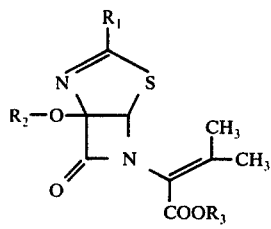

with a halogenating agent selected from N-halogenophthalimide, N-halogenosuccinimide, N-halogenohydantoin, and N-halogenocaprolactam.

8. A process for the preparation of compound of the formula:

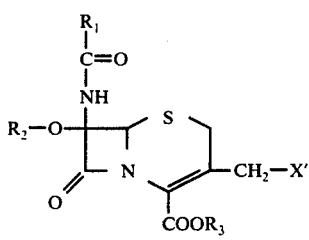

comprising dissolving a compound according to claim 1 in a conventional solvent to form a solution, then allowing said solution to stand at ambient temperature.

9. The compound of claim 1 wherein
$R_1$ is methyl, ethyl, phenoxy methyl, methyl phenoxy methyl, or benzyl,
$R_2$ is methyl or ethyl, and
$R_3$ is t-butyl, methyl, or diphenyl methyl.

10. A process for the preparation of a compound according to claim 9, which comprises treating a compound of the formula:

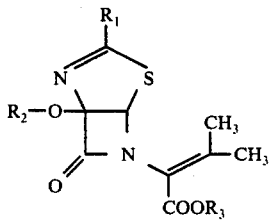

with a halogenating agent selected from N-halogenophthalimide, N-halogenosuccinimide, N-halogenohydantoin, and N-halogenocaprolactam.

11. A process for the preparation of compound of the formula:

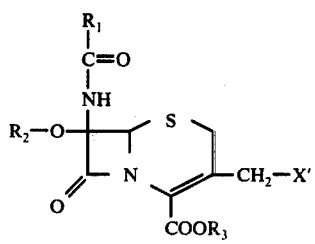

comprising dissolving a compound according to claim 9 in a conventional solvent to form a solution, then allowing said solution to stand at ambient temperature.

12. The compound of claim 9 wherein
$R_1$ is ethyl or benzyl,
$R_2$ is methyl,
$R_3$ is H, and
$X'$ is H.

13. A process for the preparation of a compound according to claim 12, which comprises treating a compound of the formula:

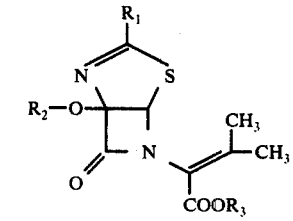

with a halogenating agent selected from N-halogenophthalimide, N-halogenosuccinimide, N-halogenohydantoin, and N-halogenocaprolactam.

14. A process for the preparation of compound of the formula:

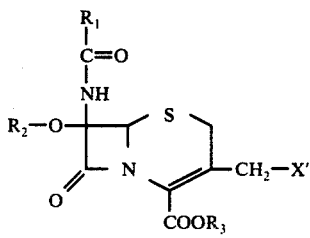

comprising dissolving a compound according to claim 12 in a conventional solvent to form a solution, then allowing said solution to stand at ambient temperature.

* * * * *